United States Patent [19]
Gold

[11] 4,328,246
[45] May 4, 1982

[54] ANTI WALKER 256 CARCINOMA AGENT AND COMBINATION THEREOF

[76] Inventor: Joseph Gold, 127 Edgemont Dr., Syracuse, N.Y. 13214

[21] Appl. No.: 179,890

[22] Filed: Aug. 20, 1980

Related U.S. Application Data

[60] Division of Ser. No. 66,442, Aug. 14, 1979, abandoned, which is a continuation-in-part of Ser. No. 582,666, Jun. 2, 1975, abandoned.

[51] Int. Cl.³ .................... A61K 31/235; A61K 33/02
[52] U.S. Cl. ...................................... 424/308; 424/166
[58] Field of Search ............................... 424/166, 308

[56] References Cited
PUBLICATIONS

Chemical Abstracts 74: 110208j, (1971).
Weitzen et al, Z. Physiol. Chem. 348, pp. 433–442.

Primary Examiner—Jerome D. Goldberg
Attorney, Agent, or Firm—Henry P. Stevens

[57] ABSTRACT

Clofibrate which lowers blood triglycerides has been found to be an affective anti Walker 256 carcinoma agent and when combined with hydrazine sulfate therapy the inhibition of growth of malignant Walker 256 carcinoma is outstanding.

3 Claims, No Drawings

ANTI WALKER 256 CARCINOMA AGENT AND COMBINATION THEREOF

CROSS REFERENCE TO RELATED APPLICATIONS

This application is a division of U.S. Ser. No. 66,442 filed Aug. 14, 1979 which in turn was a continuation-in-part of U.S. Ser. No. 582,666 filed June 2, 1975 both abandoned.

BACKGROUND OF THE INVENTION

Many different types of chemical compounds have been used in the past to treat malignant Walker 256 carcinoma. Examples of such compounds are the nitrogen mustards, estrogen, insulin, tolbutamide, fluorouracil and the biguanides. The exact mode of action encountered in such chemotherapy has never been determined and the degree of success has been nominal.

In my U.S. Pat. No. 4,110,437 issued Aug. 29, 1978, hydrazine sulfate is shown to be effective in reducing and retarding cancerous cachexia in humans even in the absence of tumor reduction. Nevertheless, the search still continues for more potent and less toxic compounds which can be added to our armamentarium in the never ending struggle to inhibit the growth of malignant Walker 256 carcinoma.

SUMMARY OF THE INVENTION

It has now been discovered that clofibrate which chemically is ethyl 2-(papachlorophenoxy)-2-methyl propionate is an anti Walker 256 carcinoma agent alone and even more effective when combined with hydrazine sulfate and administered parenterally or orally to a living host afflicted with Walker 256 intramuscular carcinoma. Although clofibrate is a known anti-hyperlipidemic agent, its Walker 256 carcinoma action has never been recognized. When clofibrate is added to hydrazine sulfate and given orally to mammals with such carcinomas, abrupt objective inhibition of the growth of said carcinomas is observed.

DESCRIPTION OF THE PREFERRED EMBODIMENTS

Clofibrate can be formulated with solid carriers such as talc, corn starch or stearic acid and compressed into tablets or gelatin capsules for oral administration. It is commercially available in 500 milligram capsules from the Ayerst Laboratories division of American Home Products Corporation, 685 Third Avenue, New York, NY, 10017. Since clofibrate is a colorless oil boiling at 150° C. at 200 millimeters pressure and insoluble in water but readily soluble in alcohol, benzene or chloroform, it can be suspended or emulsified in sterile, aqueous, saline solution and administered parenterally if desired. Clofibrate can also be administered as the sodium salt of the acid rather than the ethyl ester. Hydrazine sulfate can be formulated and administered in a similar manner.

As an antitumor agent in animals, the dosage of clofibrate is 500 mg/kg given daily orally or parenterally. The normal dosage of hydrazine sulfate in animals is 20 to 80 mg/kg given orally or parenterally daily. In animals, a good dosage regime includes 500 mg/kg of clofibrate daily and 32 mg/kg or more of hydrazine sulfate daily as an intraperitoneal injection over a period of 5 to 5 days.

The following examples set forth the best modes of carrying out the present invention.

EXAMPLE 1

In a series of tests, clofibrate and hydrazine sulfate were used alone and in combination to ascertain their growth inhibiting effects on Walker 256 carcinoma. The mammals used were Sprague Dawley female rats weighing about 70 grams each. Ten rats were used for each compound and the combination at the dosages indicated and ten rats served as controls.

On day 1, five million cells of Walker 256 intramuscular carcinoma in a volume of 0.2 ml. were injected into one thigh of each rat. On days 3–6, treatment was administered intraperitoneally at the dosages specified. The control rats were injected with saline solution only.

On day 7, the animals were all sacrificed and both lower extremities were removed. The difference in weight between the tumor thigh and the contralateral thigh was used as the weight of the tumor. Weights at the beginning and end of each test were indicative of possible drug toxicity and recorded as average weight change (AWC) or the net animal weight gain or loss minus the weight of the tumor. All animals were maintained on standard laboratory chow and water. Tumor inhibition was measured as T/C or the ratio of the tumor weight of the treated animals divided by the tumor weight of the control animals. The results are shown in the table below wherein the percent inhibition of the growth of the tumor is the reciprocal of the T/C value.

| Agent Used | Dosage mg/kg | AWC mg. | Tumor Size(mg) | T/C Ratio | Tumor Inhibition |
|---|---|---|---|---|---|
| Clofibrate | 500 | 7.1 | 6.4 | .74 | 26% |
| Hydrazine Sulfate | 32 | 12.2 | 4.9 | .57 | 43% |
| Clofibrate plus Hydrazine Sulfate | 500/32 | 2.1 | 2.7 | .31 | 69% |
| Control | — | 4.5 | 8.6 | — | — |

There were no deaths at any of the dosages employed which indicates that gross toxicity was virtually nil. From the foregoing data, it is apparent that while clofibrate alone is an antiWalker 256 carcinoma agent, in combination with hydrazine sulfate it becomes a highly effective adjunctive agent.

What I claim is:

1. A method of treating malignant Walker 256 carcinoma tumors which comprises internally administering to a mammal so afflicted ethyl 2-(parachlorophenoxy)-2-methyl propionate in a dosage sufficient to inhibit the growth of said tumors.

2. A method as in claim 1 in which said propionate is administered orally at a dosage of from about 500 to 1000 mg/kg of body weight daily.

3. A method as in claim 1 in which said propionate is administered parenterally at a dosage of about 500 mg/kg daily.

* * * * *